(12) United States Patent
Mohamed et al.

(10) Patent No.: US 12,721,916 B2
(45) Date of Patent: Sep. 1, 2026

(54) SYSTEM AND METHOD FOR PREVENTION OF CORROSIVE BIOFILM FORMATION IN PETROLEUM HOLDING OR CARRYING STRUCTURES

(71) Applicants: Hossam Abdel Salam El Sayed Mohamed, Ottawa (CA); Houda Abdul Rahman M. Al Mansour, Ottawa (CA); Saadoun Saad S. Alsaadoun, Al-Mubarraz (SA); Muneera Saadoun S. Alsaadoun, Al-Mubarraz (SA)

(72) Inventors: Hossam Abdel Salam El Sayed Mohamed, Ottawa (CA); Houda Abdul Rahman M. Al Mansour, Ottawa (CA); Saadoun Saad S. Alsaadoun, Al-Mubarraz (SA); Muneera Saadoun S. Alsaadoun, Al-Mubarraz (SA)

( * ) Notice: Subject to any disclaimer, the term of this patent is extended or adjusted under 35 U.S.C. 154(b) by 448 days.

(21) Appl. No.: 18/225,310

(22) Filed: Jul. 24, 2023

(65) Prior Publication Data

US 2024/0123101 A1 Apr. 18, 2024

Related U.S. Application Data

(60) Provisional application No. 63/415,781, filed on Oct. 13, 2022.

(51) Int. Cl.
*A61L 2/03* (2026.01)
*A61L 2/26* (2006.01)
(Continued)

(52) U.S. Cl.
CPC *A61L 2/03* (2013.01); *A61L 2/26* (2013.01); *B08B 9/0321* (2013.01); *B08B 17/06* (2013.01); *B08B 2209/032* (2013.01)

(58) Field of Classification Search
CPC . A61L 2/26; A61L 2/03; B08B 9/0321; B08B 17/06
See application file for complete search history.

(56) References Cited

U.S. PATENT DOCUMENTS

2020/0378012 A1 12/2020 Tomoe

FOREIGN PATENT DOCUMENTS

| | | | |
|---|---|---|---|
| CN | 104879067 | A | 9/2015 |
| CN | 107654739 | A | 2/2018 |

(Continued)

OTHER PUBLICATIONS

English translation of CN-113072861-B (Year: 2022).*
(Continued)

*Primary Examiner* — Sean E Conley
(74) *Attorney, Agent, or Firm* — Caesar Rivise, PC

(57) ABSTRACT

A hollow steel structure for carrying or holding liquid petroleum. The structure has an inner surface that is coated or lined with a piezo-electric material for precluding or minimizing bacterial biofilm-based corrosion. The method entails precluding or minimizing bacterial biofilm-based corrosion of a hollow steel structure that will be exposed to a flow of liquid petroleum by applying a piezo-electric material coating on it. In addition, the method may entail subjecting the hollow structure to the application of an agent for blocking and disrupting communication between the bacterial cells in the biofilm and/or an agent for blocking exocytosis among the bacteria cells of the biofilm.

11 Claims, 7 Drawing Sheets

(51) Int. Cl.
*B08B 9/032* (2006.01)
*B08B 17/06* (2006.01)

(56) References Cited

FOREIGN PATENT DOCUMENTS

| | | | | |
|---|---|---|---|---|
| CN | 113072861 B | * | 5/2022 | ............... C09D 5/18 |
| CN | 217559372 U | | 10/2022 | |
| WO | 2005111080 A2 | | 11/2005 | |

OTHER PUBLICATIONS

Dake Xu and Tingyue Gu, "The War against Problematic Biofilms in the Oil and Gas Industry," Journal of Microbial & Biochemical Technology, 2015, 7:5, DOI: 10.4172/1948-5948.1000e124, 2 pages.
International Search Report for PCT/IB2023/058258 dated Nov. 27, 2023.
Woo, D. H. et al. "Inhibitors of synaptic vesicle exocytosis reduce surface expression of receptors"., Animal Cells and Systems, 2020, vol. 24, No. 6, pp. 341-348 abstract; p. 343.

* cited by examiner 20E
20A
2
20B
20E
20
2
20F
20C
20D 20
20A
20F
20D

SYSTEM AND METHOD FOR PREVENTION OF CORROSIVE BIOFILM FORMATION IN PETROLEUM HOLDING OR CARRYING STRUCTURES

CROSS-REFERENCE TO RELATED APPLICATIONS

This utility application claims the benefit under 35 U.S.C. § 119(e) of Provisional Application Ser. No. 63/415,781, filed on Oct. 13, 2022, entitled Prevention Of Corrosive Biofilm Formation In Petroleum Carrying Pipelines, Corrosive Biofilm Resistant Pipelines For Carrying Petroleum And Methods Of Use Thereof, the entire disclosure of that provisional application is incorporated by reference herein for all purposes.

FIELD OF THE INVENTION

This invention relates generally to bacterial biofilm-based corrosion prevention, and more methods of preventing or inhibiting biofilm-based corrosion in petroleum pipelines and other conduits or hollow structures carrying flowing oil, and bacterial biofilm corrosion resistant pipelines and other hollow structures for carrying flowing liquid petroleum, and methods of use thereof.

BACKGROUND OF THE INVENTION

Gas and oil extraction is considered one of the most successful industries worldwide and many nations consider it as the cornerstone of their national income. Biocorrosion of the steel pipes or pipelines has a great economic impact on that industry. In particular, biocorrosion is a catastrophic infection of the steel tubes or pipes of pipelines used in the petroleum industry to carry flowing petroleum (oil). This is caused by bacterial infection of the inner layers of the steel pipelines. Therefore, it is sometimes called microbiologically induced corrosion (MIC) or simply biocorrosion and is a complication resulting from the growth of a bacterial biofilm (also sometimes referred to hereinafter as simply "biofilm") on the inner surface of the steel pipe or tube. In particular, the inner surface of the steel tubes or pipes carrying the flowing liquid oil in the pipeline includes a myriad of micro-crevices, i.e., tiny irregularities, in the lining of the tubes of the pipelines. These micro-crevices act as shelters for the bacteria to protect them against a high-power stream of the flowing oil, especially in the early stage where the attachments of the bacteria to the steel are weak (as will be described later). The end-stage of this bacterial infection may lead to leakage from the affected pipeline, which necessitates its replacement. Sometimes, it may lead to incomplete blockage of the affected oil-carrying pipe or tube. The worst complication is the infection in one tube of the pipeline system may lead to its spreading to the many other tubes of the rest of the pipeline. This is simply because the current of the flowing oil runs in a linear manner, wherein a proximal tube infection may lead to the spreading of the infection to all downstream tubes of the pipeline. Such an occurrence is very expensive and difficult to be treated.

This problem is gradually being given more attention because of its huge economic impact. For example, its cost in the United States alone is multi-billion dollars per year. It must be emphasized that the longer the pipeline, the more the severity and difficulty of the infection to be treated. The longest pipelines worldwide are those present in the United States, Canada, and Russia. These pipelines are spreading throughout the landscape of each of the above countries. Moreover, the pipeline of that of Russia is spreading from Russia to the nearby neighbors of the European nations to supply them with their need for oil. On the other hand, the cost of infection may be very high even if the pipeline is relatively short provided that the amount of production is very high. An example is Aramco of Saudi Arabia where the production is massive and sometimes exceeds ten million barrels per day and is accomplished by the injection of huge amounts of seawater into the pipeline to ensure the continuous flow of the oil without interruption. The injection of the seawater presents a problem, since the seawater contains nutrition that supplies the bacteria in the pipeline and thus enables the bacteria to flourish. The injection of freshwater without bacterial nourishment is not practical. In fact, it may not even be possible given the scarcity and cost of fresh water.

Unfortunately, all the microbiological centers related to the refinery system deal with corrosion-producing biofilms of steel pipelines as if they are biofilms inside the human body. There are many differences between the biofilms of the human body and that of the tubes or pipes of the petroleum-carrying pipelines. Therefore, the wrong approach to biocorrosion in the pipeline system leads to wrong results so that the resistance to the healing of the infection of the pipeline system is almost always inevitable.

The petroleum industry has taken various approaches or modalities for preventing or ameliorating biocorrosion. However, all have failed for one reason or another.

For example, antibiotic therapy is considered the main line of treatment for the infected tube. This could be beneficial in the very early stage of treatment where the bacterial cells are in the planktonic form. However, once these bacteria cells assemble with each other to form the biofilm, the antibiotics become gradually ineffective till they become completely useless. This means the resistance to antibiotics is gradual. They always add a new stronger antibiotic which also becomes ineffective later. Therefore, their strategy is to add more and more antibiotics with a gradual increase in the dose of each. Unfortunately, failure of the procedure is almost always inevitable and the causes of failure will be explained later.

It must be noted that antibiotic therapy has two distinctive features that make it different from the human biofilm. The first is that in a petroleum pipeline system, there is no immune system to help in the defeat of the bacteria, as is the case in humans. The second distinctive feature is that there would be no upper limit of toxicity in the pipeline system. Therefore, antibiotics can be added in numbers and doses without fear of toxic limitations. The only drawback is that antibiotic therapy would be gradually less effective until it becomes useless. The possible methods of resistance of biofilms to antibiotics include the expelling of the antibiotics outside the biofilm. Chelating agents of antibiotics with DNA of the dead bacterial cells, e.g., Tobramycin, an antibiotic of the aminoglycoside group, if it has been used. The plasma of extra-cellular polymeric substance (EPS) has been used to act as a diluting agent that prevents the toxic effect of the antibiotic, wherein the bacterial cells can enter into a stationary state that reduces all the metabolic processes to a minimum, so they become resistant to all harsh environmental factors, including antibiotics. Paradoxically, antibiotic administration may even by itself enhance the conversion of the planktonic form of bacterial cells to the biofilm or (sessile) form as will be explained later.

Another treatment modality to reduce bacterial biofilm formation involves nitrogen gas administration so that the nitrogen gas replaces the oxygen in the seawater to deprive aerobic bacteria of their oxygen need. Therefore, in theory, the bacteria should stop multiplying and spreading. Unfortunately, this may not prove to be the case in actual practice. In this regard, while the nitrogen may deprive the bacterial cells of their oxygen need, it may enhance the biofilm formation at the same time since the more unfavorable conditions for the bacterial cells, the more they tend to assemble with each other to form a biofilm. Thus, the possibility of biocorrosion would be increased.

Another treatment modality to reduce biofilm formation involves the replacement of the infected segment of the pipeline system. This may be the only symptomatic treatment of a damaged tube that shows biocorrosion with or without signs of leakage. Sometimes corrosion does not occur, but the creation and growth of biofilm itself induce a partial obstruction of the pipeline tube. This may be even more difficult to treat. It is presented by the narrowing of the downstream of oil. Moreover, it becomes much more difficult if the obstruction is in multiple zones. This causes a loss of energy in the over-pushing of the obstructed tubal system. This is because the detection of the exact site of the partial obstruction may necessitate extensive and hence, expensive, investigations. Furthermore, the missing of even a small, infected segment may act as a new septic focus. Thus, the tubal system would be re-infected again and again establishing a vicious circle that needs to be broken.

Heretofore, all the already present lines of treatment for the infected tubal system of the petroleum industry fail in one way or another since they do not address the root causes of the biocorrosion.

In contradistinction, the subject invention takes the approach that the best method of fighting the biocorrosion of the tubal system of the pipeline is at its starting point. In particular, the subject invention does not allow the biofilm to be formed in the first place, rather than wait until the occurrence of the biocorrosion to deal with it. To that end, the subject invention addresses the root causes and the molecular mechanics of biocorrosion, the spreading of infection, and the mechanism of bacterial resistance in the pipeline system. That action is achieved by three lines of treatment of the subject invention. They are, in order of importance: (1) hindering the attachment of the basal layer of the biofilm with the inner wall of the pipeline; (2) blockage and disruption of the communication between the bacterial cells inside the biofilm; and (3) blockage of exocytosis. Those three lines of treatment will be described in detail later. Suffice for now to state that they provide a simple, yet viable strategy to prevent the formation of biocorrosion of steel pipelines in the first place.

SUMMARY OF THE INVENTION

One aspect of this invention is a method of precluding or minimizing bacterial biofilm-based corrosion of a carrier or holder of liquid petroleum. The method comprises providing a hollow structure that will be exposed to a flow of liquid petroleum. The hollow structure is formed of steel and has an inner surface. The inner surface is coated or lined with a piezo-electric (hereinafter "PZE") material.

In accordance with one aspect of the method of this invention, the piezo-electric material is selected from the group comprising: silicon oxide, ceramic, polyvinylidene fluoride (PVDF), or zinc oxide.

In accordance with another aspect of the method of this invention, the inner surface of the hollow structure includes micro-crevices.

In accordance with another aspect of the method of this invention, the micro-crevices have a width of less than approximately 10 μM or greater than approximately 50 μM.

In accordance with another aspect of the method of this invention, the method additionally comprises applying a force to the liquid petroleum to result in turbulent flow in the micro-crevices which are greater than approximately 50 μM.

In accordance with another aspect of the method of this invention, the piezo-electric material is at least approximately 2 mm thick.

In accordance with another aspect of the method of this invention, the carrier comprises a petroleum pipeline, wherein the hollow structure comprises a pipe or tube.

In accordance with another aspect of the method of this invention, the method comprises causing said liquid petroleum to flow through said pipe or tube.

In accordance with another aspect of the method of this invention, the biofilm includes bacterial cells, and wherein the method additionally comprises blocking and disrupting communication between the bacterial cells in the biofilm.

In accordance with another aspect of the method of this invention, the blocking and disrupting communication between the bacterial cells in the biofilm is accomplished by the use of an agent of one or more of acyl-homoserine lactone analogs, lactonases, and acylases.

In accordance with another aspect of the method of this invention, the bacteria cells are capable of exocytosis, and wherein said method additionally comprises blocking exocytosis among the bacteria cells.

In accordance with another aspect of the method of this invention, the blocking exocytosis among the bacteria cells is accomplished by the use of an agent one or more of bafilomycin, botulinum toxin B, and tetanus toxin.

Another aspect of this invention is a structure for carrying or holding liquid petroleum. The structure comprises a hollow member and a coating or lining. The hollow member has an inner surface formed of steel. The coating or lining is a piezo-electric material on the inner surface of the hollow member.

In accordance with one aspect of the structure of this invention, the piezoelectric material is selected from the group comprising: silicon oxide, ceramic, polyvinylidene fluoride (PVDF), or zinc oxide.

In accordance with another aspect of the structure of this invention, the inner surface of the hollow member includes micro-crevices.

In accordance with one aspect of the structure of this invention, the micro-crevices have a width of less than approximately 10 μM or greater than approximately 50 μM.

In accordance with another aspect of the structure of this invention, the piezo-electric material is at least approximately 2 mm thick.

In accordance with another aspect of the method of this invention, the carrier comprises a petroleum pipeline, wherein the hollow structure comprises a pipe or tube.

DETAILED DESCRIPTION OF THE PREFERRED EMBODIMENT

Figures 1, 2:
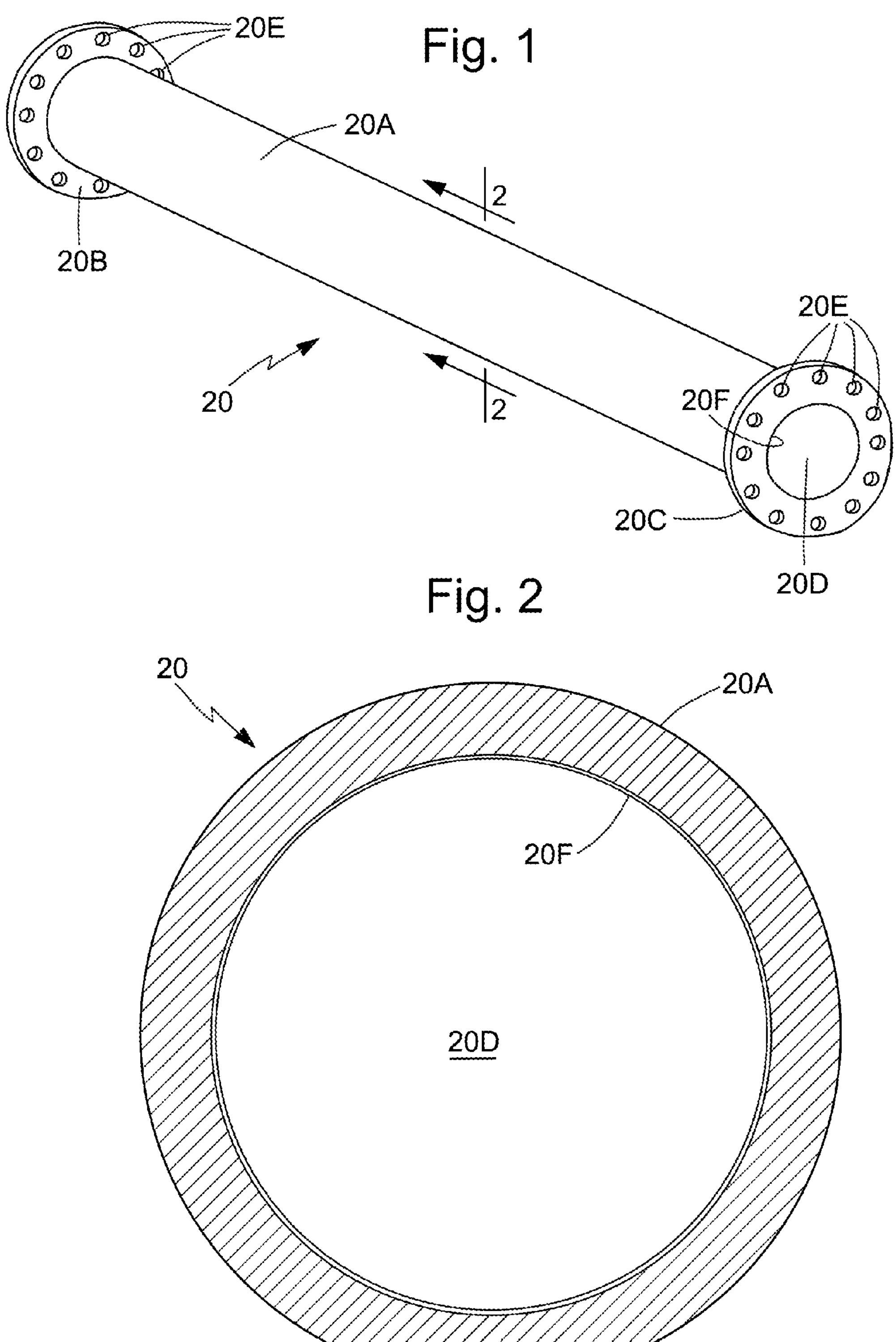
FIG. 1 is an isometric view of one exemplary liquid petroleum carrying structure, e.g., an oil pipeline, constructed in accordance with this invention.
FIG. 2 is enlarged, but not to scale, a cross-sectional view of the portion of the pipeline taken along lines 2-2 of FIG. 1.

Referring now to the various figures of the drawing wherein like reference characters refer to like parts, there is shown in FIG. 1 at a section of a bacterial biofilm corrosion-resistant tube or pipe 20 for carrying liquid petroleum (e.g., oil) constructed in accordance with one aspect of this invention. That tube section basically comprises a hollow tubular body 20A having a flange 20B at one end and a flange 20C at the other end and with a central passageway 20D extending the length of the tube section between the flanges 20B and 290C. The flanges 20B and 20C enable the tube section 20 to be connected to other flanged tube sections to form a petroleum pipeline. To that end, each flange includes a plurality of equidistantly spaced holes 20E for receipt of respective threaded fasteners, e.g., bolts (not shown), extended therethrough and secured together by respective nuts (not shown) on the bolts.

In accordance with one aspect of this invention, the inner surface of the passageway 20D is in the form of a coating or lining 20F of a piezo-electric material.

Before describing the details of the piezo-electric coating or lining 20F of the pipe or tube is shown in FIG. 1, and any other pipe or tube for carrying flowing petroleum having a piezo-electric material coating or lining constructed in accordance with this invention, the method of making that pipe or tube and the method of using it, a brief discussion of bacteria, the culprit of bio-corrosion, and the molecular mechanics of biofilm formation in the petroleum industry is in order and will now be discussed.

There are two forms of bacteria, namely, the planktonic form and the biofilm form. The planktonic form is illustrated in the area designated as A in FIG. 3A and is a free form of the bacteria. Each bacterial cell acts as a separate entity. Therefore, the bacterial cells do not communicate with each other. These cells are highly susceptible to antibiotics and other harsh environmental factors and can be easily killed. In contradistinction, the biofilm form is an aggregation of many bacterial cells that form a sessile structure. The bacterial cells synchronize with each other to resist antibiotics and all other harsh environmental factors. This can be accomplished via different mechanisms which include: expelling of the antibiotics outside the biofilm; (2) the DNA of dead bacteria acting as a chelating agent for certain antibiotics, e.g., tobramycin of aminoglycoside family, if it is applied; (3) the extracellular polymeric substance (EPS) acts as a diluting medium for the antibiotic if it is applied; and (4) the formation of "persister" cells that are resistant to both the antibiotics and all other harsh environmental factors.

Persister cells go through a stationary state where they reduce their metabolism to a minimum. Subsequently, they can resist antibiotics and all other harsh environmental factors by several orders of magnitude more than that of the planktonic cells.

Insofar as the molecular mechanics of biofilm formation in petroleum pipelines is concerned the mechanism of the resistance of biofilm to antibiotics is a function of the factors of Microbial Surface Component Recognition Adhesive Matrix Molecule (hereinafter "MSCRAMM"), Extra-cellular Polymeric Substance (hereinafter "EPS"), Quorum Sensing (hereinafter "QS"), persister cells, the mode of flow of the oil inside the pipeline, and the forces that control the biofilm, as will be explained immediately below.

Figure 3A:
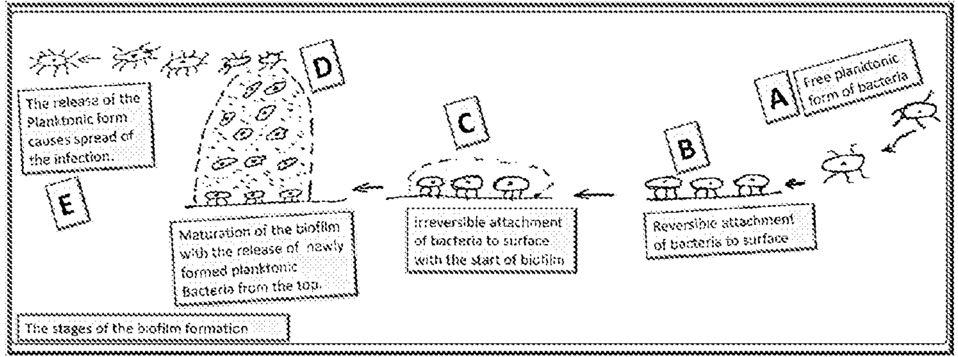
FIG. 3A is a sketch illustrating the stages of bacterial biofilm formation, which will be described later, and which are: (A) free planktonic form of bacteria; (B) reversible attachment of bacteria with the inner surface of the tubal system; (C). irreversible attachment of bacteria with the start formation of the biofilm, i.e., extra-cellular polymeric substance (EPS); (D) maturation where the biofilm (sessile) of the bacterial aggregate is formed; and (E) the release of the new planktonic form of bacteria from the top of biofilm to spread the infection.
Figure 3B:
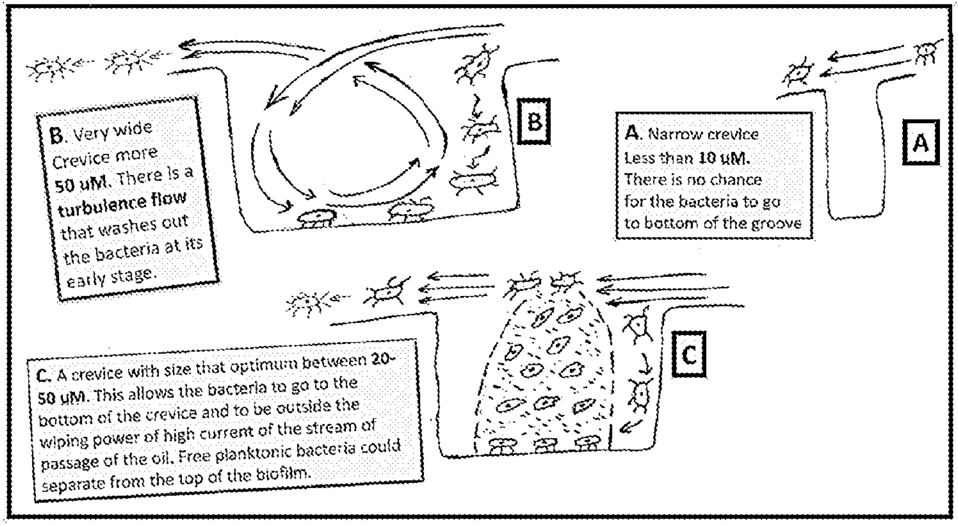
FIG. 3B is a sketch illustrating the effect of the size of the micro-crevices in the inner surface of the pipe or tube carrying the flowing liquid petroleum on bacterial biofilm formation in those micro-crevices and contiguous inner surfaces of the pipe or tube carrying the flowing liquid petroleum as will be described later.
Figure 3C:
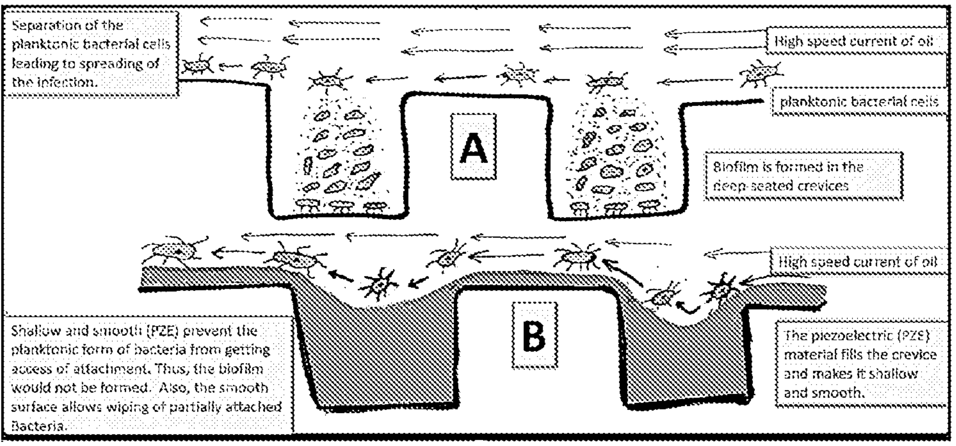
FIG. 3C is a sketch illustrating the effect of the use of a piezo-electric material coating or lining on the inner surface of the pipe or tube carrying the flowing liquid petroleum on the bacterial biofilm formation as will be described later.
Figure 3D:
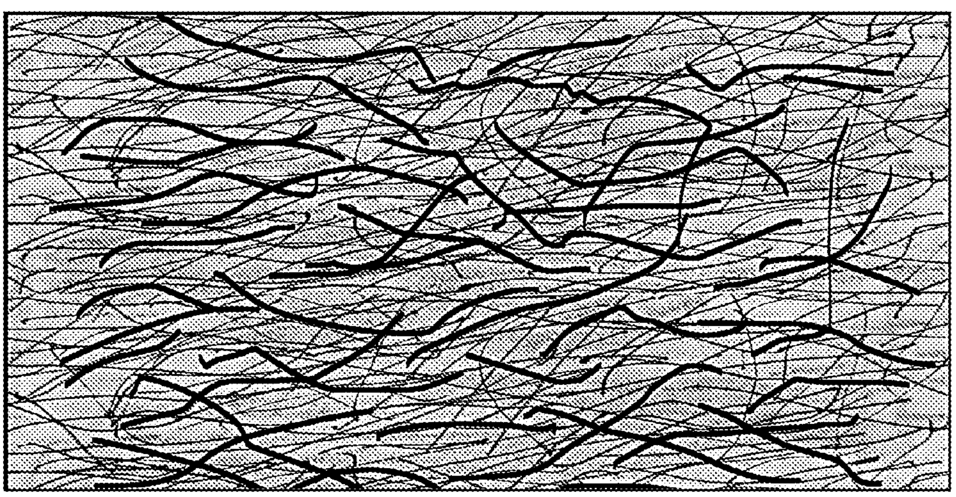
FIG. 3D is a sketch of a very greatly enlarged inner surface of the pipe or tube carrying the liquid petroleum illustrating the micro-crevices in that inner surface.
Figure 3E:
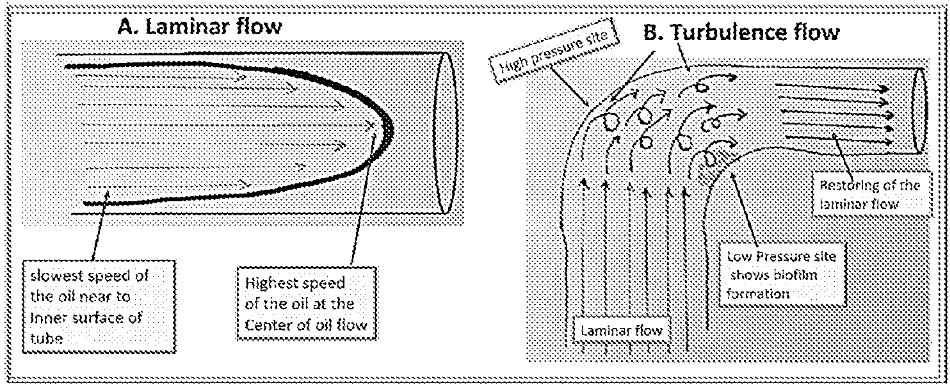
FIG. 3E is a sketch illustrating the laminar flow of liquid petroleum through a straight section of a liquid petroleum-carrying pipe or tube and illustrating turbulence or turbulent flow through an angled section of the liquid petroleum-carrying pipe or tube as will be described later.
Figure 3F:
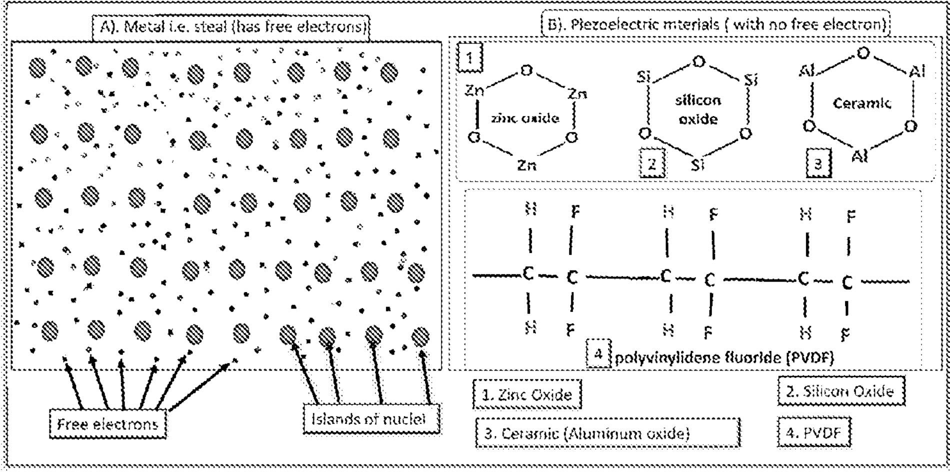
FIG. 3F is a sketch illustrating the difference between metals and piezo-electric materials insofar as free electron formation is concerned, this will be described later.
Figure 3G:
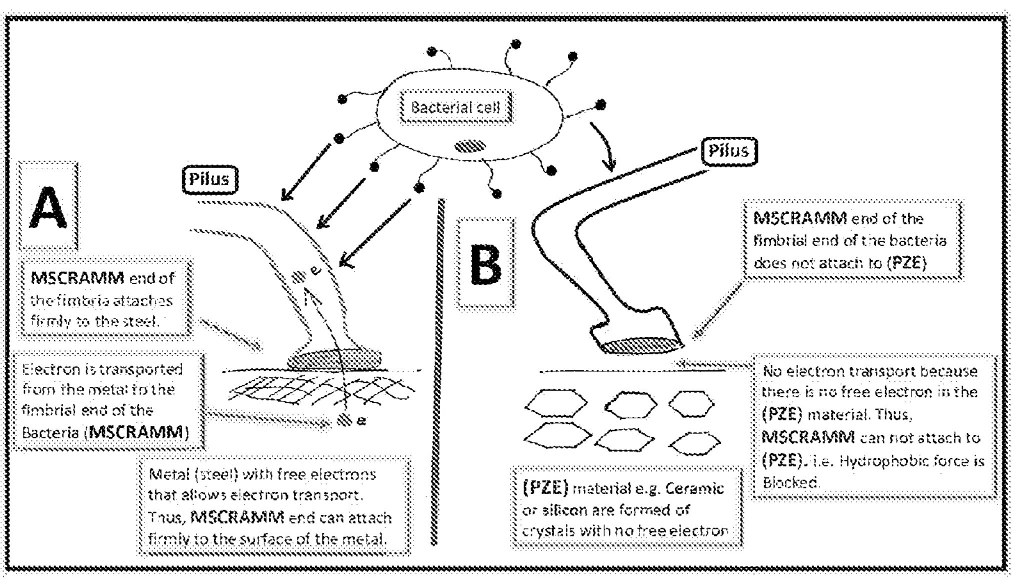
FIG. 3G is a sketch illustrating a comparison between the fimbrial or the pilar end attachment of a bacterial cell to a conventional steel liquid petroleum carrying pipeline, and the failure of such an attachment if the inner surface of the petroleum carrying tube is coated with a piezo-electric material in accordance with this invention, as will be described in detail later.

MSCRAMM are the attachment sites at the ends of fimbriae or pili, as illustrated in the area designated as A in FIG. 3G, of certain bacteria, e.g., Staph. *Aureus, Pseudomonas, proteus, Klebsiella, E. coli, enterococcus*, and many others. These sites produce a strong attachment, via the hydrophobic force, to the surface of the metal. This depends on electron transport between the metallic surface and MSCRAMM of fimbriae or pili of the bacteria. The attachment passes through different phases, namely reversible attachment, irreversible attachment, and maturation.

Reversible attachment is illustrated in the area designated as B in FIG. 3A where the attachment is weak and can be easily washed out by the strong current of rapidly passing oil, as will be described later. Thus, the biofilm needs further protection via the micro-crevices of the inner wall of the pipe or tube-like shown in FIG. 3D. If the surface is smooth or better ultrasmooth, like that of a piezo-electric coating material constructed in accordance with this invention and which will be described in detail later, the nascent biofilm could be washed out and the process would be aborted in its early stage like illustrated in the area designated as B in FIG. 3C. If, however, the biofilm succeeds to survive, it would reach the next stage which is irreversible attachment and is illustrated in the area designated as C in FIG. 3A. The irreversible attachment is where the biofilm becomes very strong to get out of the micro-crevices and succeeds to resist the shearing power of the high-speed current of the flowing oil without being washed out of the micro-crevices. The biofilm would then enter the next phase, which is the maturation stage and is illustrated in the area designated as D in FIG. 3A. The maturation stage is where the biofilm becomes mature and even starts to spread the infection downstream as illustrated in the area designated as E in FIG. 3A. This stage is very difficult to be treated by antibiotics or physically by the high-speed current of the flowing oil.

The mechanics of the electron transport at MSCRAMM is the fundamental process for the attachment between the MSCRAMM of the bacteria and the inner surface of the pipes or tubes of the pipeline carrying the oil. Electron transport is associated with the hydrophobic force which is the cause of attachment between the biofilm and the inner surface of the tube. It must be noted that metals, including steel, have free electrons. The microscopic structure of the metals consists of islands of positive nuclei surrounded by seas of free electrons as illustrated in the area on the left side of FIG. 3F. The free electrons are the reason for the excellent conduction of metals to heat and electricity. Moreover, it is the cause of biofilm formation via the transmission of electrons from the metallic surface to the MSCRAMM of the bacterial ends. This process is very important in the maturation of the biofilm, i.e., the transmission of the biofilm from one stage to another, i.e., the reversible, irreversible, and subsequent mature phases of the biofilm. This cannot be accomplished in the absence of the free electrons.

Figure 3H:
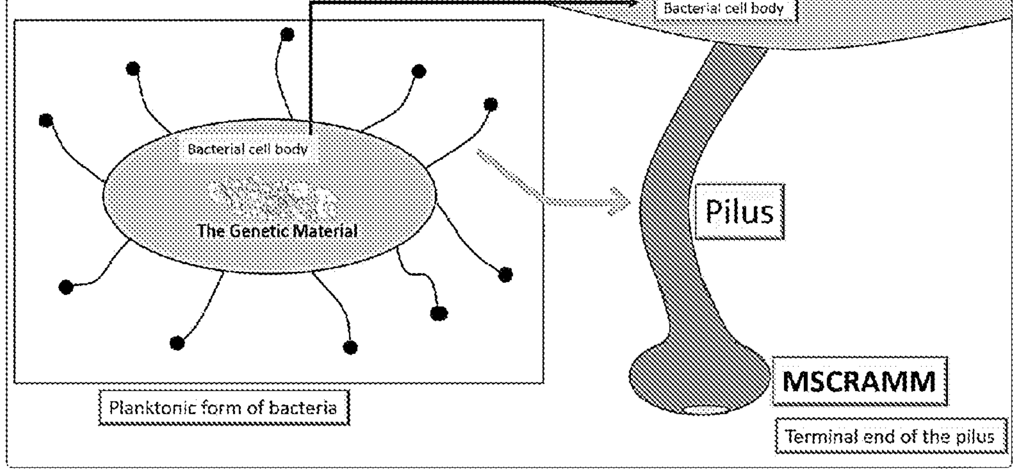
FIG. 3H is a sketch illustrating bacterial pilus anatomy.
Figure 3I:
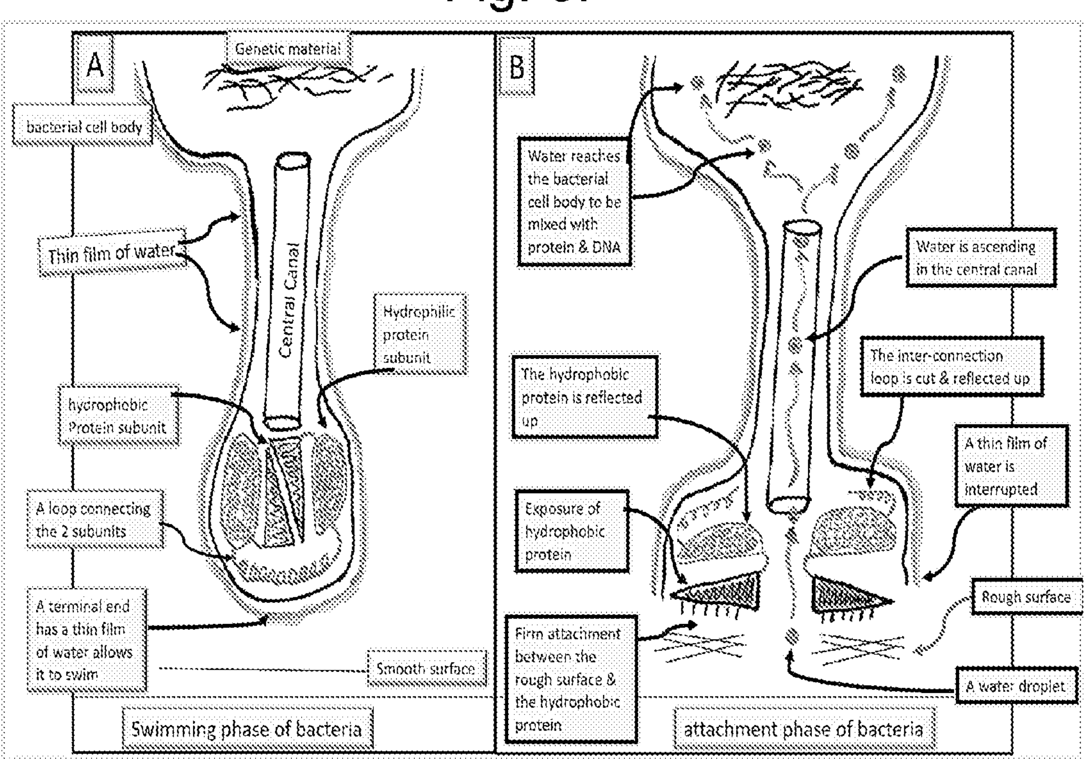
FIG. 3I is a sketch illustrating the scheme of the pilus and its mechanics.
Figure 3J:
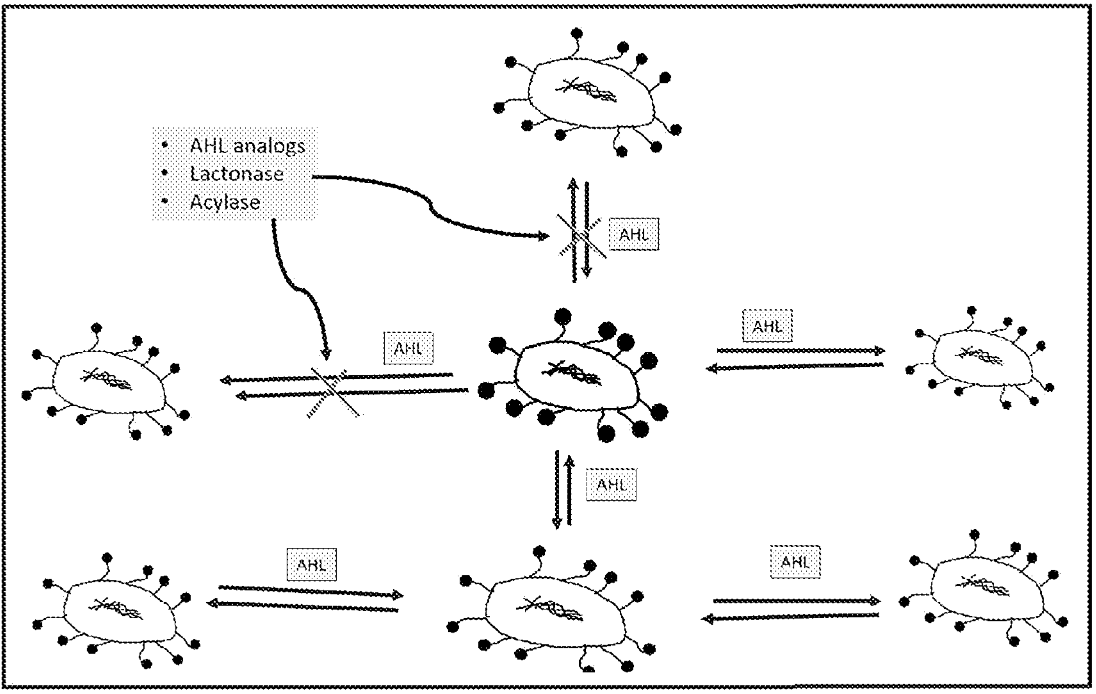
FIG. 3J is a sketch illustrating the blockage of attachment of Acyl Homoserine Lactone (AHL).
Figure 3K:
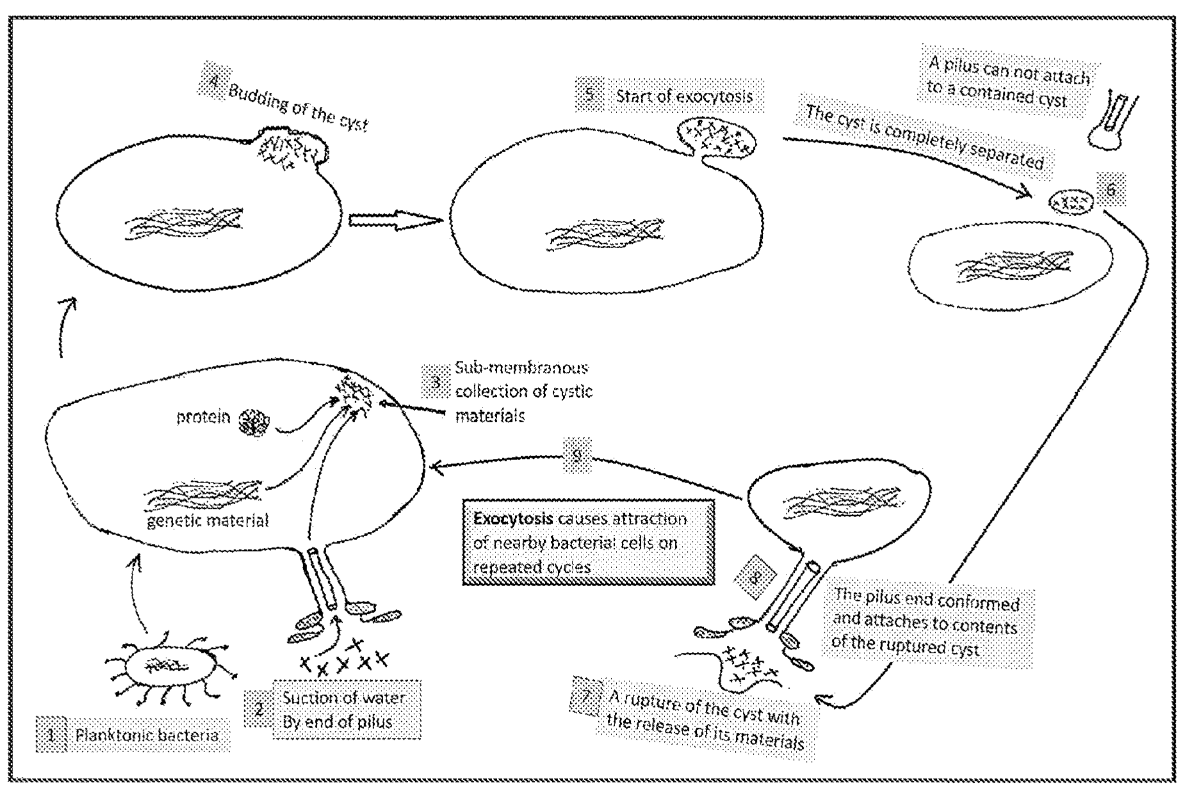
FIG. 3K is a sketch illustrating exocytosis causing the attraction of nearby bacterial cells.
Figure 3L:
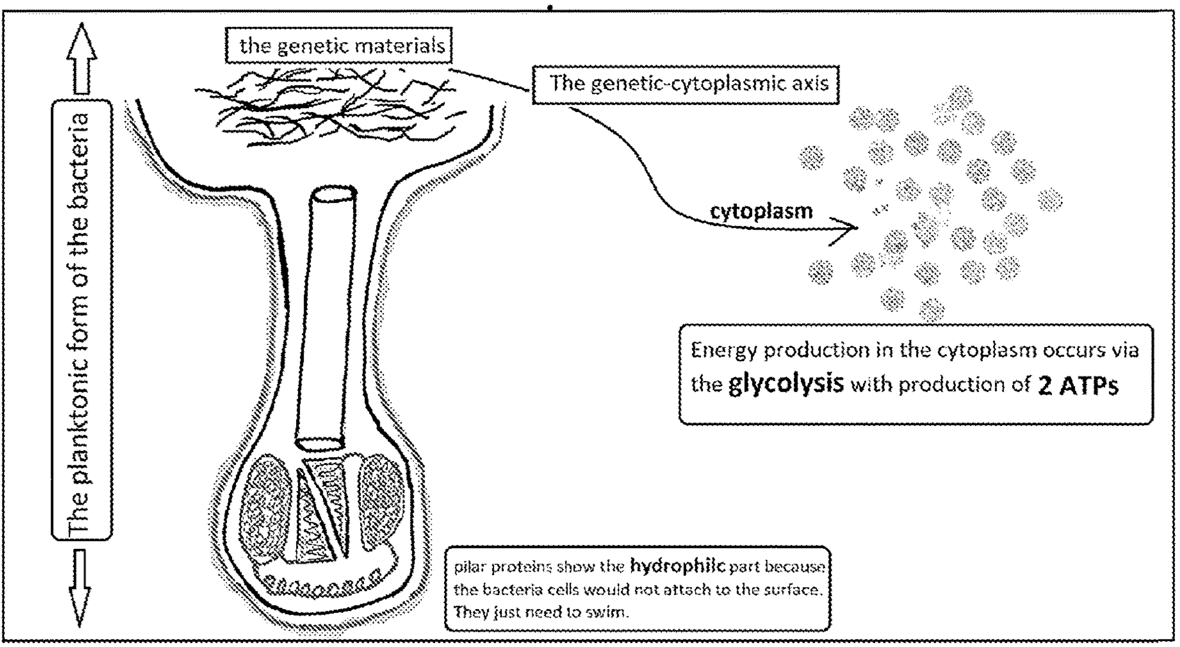
FIG. 3L is a sketch illustrating the terminal pilar proteins in the case of the planktonic form bacteria. It is associated with low energy production of two (2) ATPs (Adenosine Triphosphates) from the cytoplasm only.

The long-standing process of electron transport from the metallic end to MSCRAMM is responsible for thinning out of the wall of the steel tube at the site of a biofilm. A leakage would occur when the wall becomes very thin until the point that cannot withstand the high pressure inside the tube. The electrons are continuously sucked by the pili of the bacterial biofilm. This results in a higher concentration of positively charged nuclei in the spot related to the biofilm with a scarcity of negatively charged electrons. The positively charged nuclei repel each other and migrate to the nearby areas to maintain the electrical equilibrium between the electron and nuclei as shown in FIG. 3N, and which will be described below, because the metal substance is nothing more than positive islands of nuclei and a sea of negative electrons. The loss of these two items, in the long run, causes a gradual thinning of the wall of the metallic spot related to the biofilm.

Thus, turning to FIG. 3N it should be noted that the metals of the steel tube are formed of islands of positively charged nuclei surrounded by a sea of freely mobile negatively charged electrons. The electron transport through pili of the bacteria leaves the metallic side with a more positively charged nuclei that repel with each other. Subsequently, they migrate towards areas with more electrons. The thickness of the affected area is gradually reduced until it becomes very thin and may leak under the effect of the high pressure of oil inside the steel tube. In particular, the area designated A of FIG. 3N shows the full thickness of a steel tube that formed an island of positively charged islands of nuclei in a negatively charged sea of electrons. The area designated B of FIG. 3N shows the partial erosion of the steel tube caused by electron transport from the steel to the pilar ends of the bacteria. The area designated C of FIG. 3N shows the erosion becomes very marked and the steel tube is about to leak when erosion is completed. In short, as shown in FIG. 3N, the negatively charged electrons pass through the pili of bacterial biofilm. The remaining positively charged nuclei repel with each other and some migrate to other areas. Because the metal is formed of nuclei and electrons, the migration of nuclei and the transport of the electrons lead to the thinning of the mass of the metal substance. This is simply because the two components of the metallic bond are greatly reduced in number.

As will be described in detail later, the subject invention gets the benefit of preventing biofilm erosion from occurring by the utilization of materials that have no free electrons at all, in this case, PZE materials. These materials are formed of crystals or polymers with no free electrons, as illustrated in the area on the right side of FIG. 3F. Thus, electron transport cannot be accomplished, and hydrophobic forces would be aborted, so that lining the tubes of the pipelines with a PZE material could prevent the formation of the biofilm in the first place and subsequently, biocorrosion could not occur.

The schematic anatomy of the pilus dictates the formation and maturation of the biofilm. As shown in FIG. 3H, each bacterial cell has multiple, e.g., 80-120, pili according to its type. The planktonic form swims in the medium because each pilus is fully surrounded by a thin film of water as shown in FIG. 3I. To that end, FIG. 3I illustrates the scheme of the pilus and its mechanics. Conformational changes i.e., shape and structural changes, occur in the terminal pilus and explain the mechanism of biofilm formation so that biofilm formation can be avoided. As can be seen in the area designated A of FIG. 3I, the expanded terminal end of a pilus is formed of hydrophilic (i.e., water-loving) protein that catches the thin film of water. This enables the bacteria to swim freely in the medium fully surrounded by a thin film of water wherein the surrounding surface is smooth. The pilus has a central canal that conducts the fluids and nutrition from the exterior to the bacterial cell body. There are two subunits of hydrophobic (i.e., water-hating) protein in the center of the MSCRAM. The position of this hydrophobic protein is of fundamental importance for the formation of biofilm for the following two reasons. The two subunits of the hydrophobic protein block the external opening of the central canal. Thus, they prevent the fluid from entering the bacterial cells. Therefore, the fluid which would be the future biofilm will not enter the bacterial cell in the first place as illustrated in FIG. 3I. Moreover, the two subunits of the hydrophobic protein are fully surrounded by another two subunits of hydrophilic protein. Thus, the expanded terminal end of the pilus is fully surrounded by a thin film of water that allows the bacteria to freely swim.

Conformational changes occur in the terminal pilus in the following steps as illustrated in the area designated B in FIG. 3I: (1) the hydrophobic protein is exposed towards the rough surface; (2) an electron transport from the rough surface (of metals which are rich in free electrons) to the hydrophobic protein; (3) an associated absorption of water from the medium passing through the central canal; (4) the water reaches the bacterial cell body, where it is mixed with the genetic material and the protein of the bacteria; (5) the water is expelled from the other side bacteria in the form of viscid fluid that contains the genetic and protein materials of the bacterial cell; and (6) the expelled water acts as chemotactic (i.e., attractive) factors for other bacterial cells that are crowded on these secreted vesicles. Those foregoing steps are the basis for new biofilm formation.

When the bacteria encounter a rough surface i.e., (micro-crevices) of the metallic wall, the conformational changes as stated above occur in the MSCRAMM with the following consequences. The subunits of the hydrophobic protein become exposed to the rough surface. As the hydrophobic protein hates water, the terminal end loses its thin film of water and cannot swim anymore and settle down towards that rough surface. At that time, the attachment between the bacterial cell and the surface is still weak. The two subunits of the hydrophilic proteins are reflected up as shown in area B of FIG. 3I. A series of electron transport occurs from the metallic end to the hydrophobic protein which has a great affinity to the electrons from the metallic side. This creates a firm attachment between the pili of the bacterial cell and the metallic wall. As is known electrons are negatively charged. Thus, the transfer of the electrons from the metallic side to the bacterial side at (MSCRAMM) creates an electrostatic force between the bacteria and the inner wall of the tubal system. This force is built because the bacterial end becomes relatively more negatively charged than that of the inner surface of the tube. This electrostatic force further strengthens the firm attachment of the biofilm, i.e., the stage of irreversible attachment in FIG. 3A. The terminal end of the central canal is opened to the exterior as the two subunits of the hydrophobic protein leave their positions in blocking the central canal to attach to the surface leaving the canal widely open. A fluid passes from the exterior to the bacterial cell body via the difference in the oncotic pressure which is always higher inside the bacteria cell due to its protein and genetic contents in bacterial plasma. Also, the suction of fluid occurs secondary to the electron transport from the metallic side towards the MSCRAMM side of the bacterial pilus. Furthermore, the process of suction of fluid is enhanced at the stage of biofilm by the bacterial genetic materials through the increased synthesis of more MSCRAMM proteins at the pilar terminals as will be explained later as the genetic-pilar axis. Some of the fluids are mixed with genetic and bacterial proteins. In addition, some of the fluids are secreted (expelled) on the other surface of the bacteria which is known as exocytosis as mini vesicles. Shortly, these vesicles rupture, and a viscid (mucinous) material is released on the other side of the bacterial surface. The expelled fluid acts as a chemotactic factor that attracts other bacterial cells to enter the fluid nearby the bacteria. Lastly, the biofilm is born when the bacterial number reaches a certain threshold, i.e., QS.

It must be noted that the genetic materials of the bacterial cells are not surrounded by a nuclear membrane, as in the case of mammalian, e.g., human, cells. This means that the communication between the genetic materials and the pilar proteins is simple and is not regulated by the nuclear pores. In other words, this communication is always instantaneous. This also means that the genetic materials, in the body of the bacteria, always have information about the conditions of the pilus whether its terminal end is either opened or closed. This is very important in the mechanism of resistance to antibiotics. Moreover, the genetic materials send these pieces of information to the bacterial cell membrane. The cell membrane of bacterial cells can respond by making the energy production either via oxidative phosphorylation (OxPh) or simple glycolysis according to the bacterial needs. It is known that glycolysis occurs in the cytoplasm (as illustrated in FIG. 3L) and gives a very small amount of energy, i.e., two (2) ATPs that are sufficient for the swimming bacteria. In particular, as can be seen in FIG. 3L in the case of planktonic form of the bacteria, the pilar proteins show the hydrophilic components that allow the bacteria to swim. The energy is only produced in the cytoplasm via the genetic-cytoplasmic axis, whereupon the energy produced is only two (2) ATPs. It should be noted that the pilar protein-genetic axis is not working because the hydrophobic protein is concealed. Therefore, the is no electron transport.

Figure 3M:
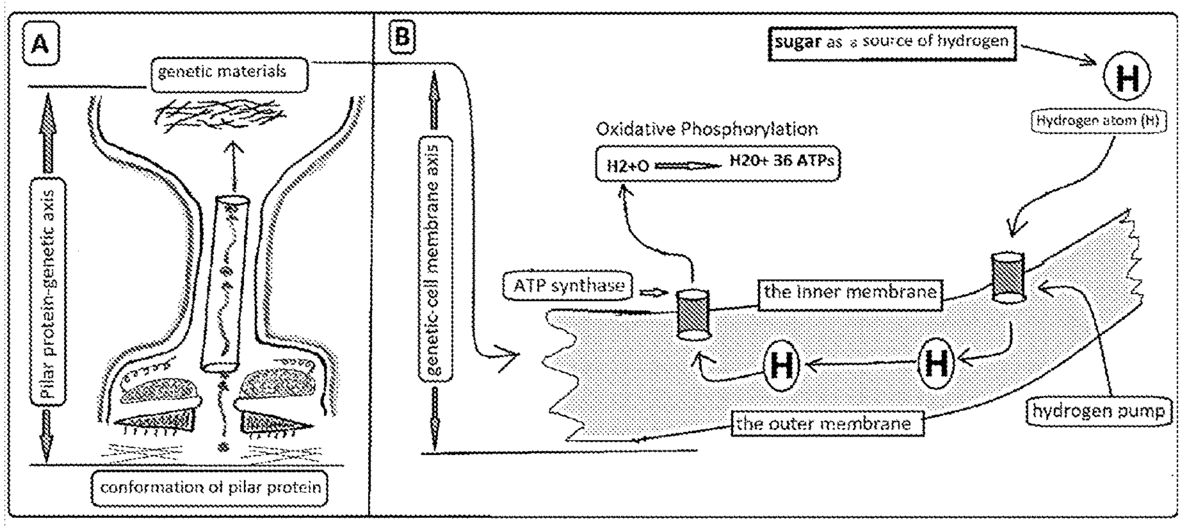
FIG. 3M is the sketch illustrating the terminal pilar protein configuration in the bacteria of the biofilm that is associated with high energy production of thirty-six (36) ATPs through Oxidative Phosphorylation (OxPh) of the cell membrane of the bacteria.
Figure 3N:
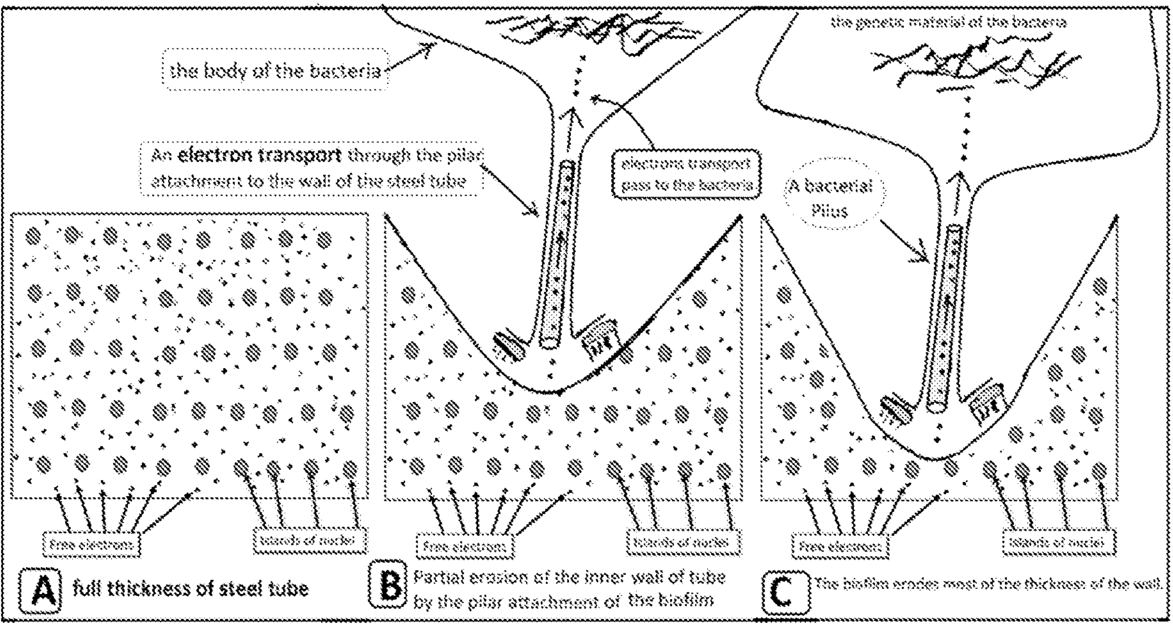
FIG. 3N is the sketch illustrating the mechanism of thinning out of the wall of the steel via electron transport.

Turning now to FIG. 3M it can be seen that in the case of biofilm formation, the bacterial cells have two axes for energy production. In particular, the left-side of the illustration of FIG. 3M designated as "A" shows the pilar protein-genetic axis which occurs after the attachment of hydrophobic proteins on the rough surface and is associated with electron transport. The right-side of the illustration of FIG. 3M designated as "B" shows the genetic-cell membrane axis which is associated with (OxPh) that occurs in the cell membrane of the bacteria and results in the production of thirty-six (36) ATPs. This surplus amount of energy is essential for biofilm formation as it is needed in the strong attachment of the bacteria, the building of the new pilar proteins that are essential for further strengthening of the attachment of the biofilm, active pumping of extra-cellular polymeric substance (EPS) from the opposite side of the attachment, and active pumping of the antibiotics out of the biofilm. Thus, the genetic material of the bacteria without a nuclear membrane act as a mediator and an organizer between the pilar proteins and the cell membrane according to the situation. The freely mobile bacterial cells need a small amount of energy and use the glycolysis process for energy production with a resultant of only 2 ATPs which is more or less sufficient for the basic needs of swimming bacteria, i.e., the planktonic form while the bacterial cells inside the biofilm need a larger amount of energy. Therefore, they use (OxPh) with resultant thirty-six (36) ATPs for the strong attachment, manufacturing of new proteins necessary for the biofilm, active pumping of the antibiotics outside the biofilm, etc.

All this can be done via the intact (pilar protein-genetic axis) and the other linked axis which is (the genetic-cell membrane axis). However, these two axes are synchronized with each other to make the biofilm, the most important step is the very early one of terminal pilar protein attachment to the rough surface. This means that failure of this step would abort all the subsequent steps and biofilm would not be formed or become weak enough to be dislodged.

From the above, it could be concluded that the structural anatomy of the terminal pilus is the most important part of biofilm formation. Therefore, to stop or even inhibit biofilm formation, one must deal with the protein structure of the MSCRAMM.

EPS constitutes a plasma fluid on the opposite side of the attachment which the bacteria secrete. The plasma fluid acts as a medium for other bacterial cells to aggregate to form biofilm. The EPS contains lipopolysaccharides (LPS), protein materials, and DNA. This medium also acts as a method of communication between the bacterial cells via Acyl-Homoserine Lactone (AHL). This medium also dilutes the antibiotic effect of the bacterial cells. The lipopolysaccharides are the remnants of the cell membrane of the dead bacterial cells that are killed by the antibiotics at the early stage when they were in the planktonic form. The living bacterial cells incorporate LPS in their cell membranes. They also absorb the genetic materials (e.g., DNA) of killed bacterial cells. Subsequently, after this incorporation, the living bacterial cells could know the information about the mechanism by which the antibiotic kills their ancestors. Accordingly, they could develop a resistance to this antibiotic. Furthermore, they spread the resistance to this antibiotic to other nearby bacterial cells via AHL, as will be explained shortly. Aftermost, the majority of the bacterial cells inside this biofilm become resistant to that antibiotic. This explains the gradual resistance of the biofilm to antibiotics.

Quorum sensing (QS) is the minimal number of bacterial cells that could coalesce to build a new biofilm. Below this number, the bacteria could not succeed to assemble a biofilm. This is why, the early stages of biofilm need shelters, i.e., micro-crevices in the metals to give protection for the bacterial cells tell they reach that threshold number that allows them to start the biofilm formation. The mechanism of the communication between bacterial cells to form a biofilm could be explained through the following steps. A recently discovered material for the communication between bacterial cells is AHL. This material allows the transmission of resistance to antibiotics between the bacterial cells as explained earlier. It is important to note that the method of communication between the bacterial cells in the biofilm occurs at the vertical and horizontal levels at the same time. This explains the fast spread of the resistance of bacterial cells to the specific antibiotic in a very short time. In other words, the early sensitive bacterial cells are killed by the antibiotic but their remnants in the form of (DNA, LPS, and proteins) transfer the data to other living bacterial cells. These living cells receive these data and respond accordingly via secreting of AHL. Therefore, the resistance would spread to all bacterial components of the biofilm. This explains why resistance to an antibiotic is inevitable to occur even though it is considered a routine treatment in the petroleum industry. As said earlier, the wrong approach always gives wrong results. Thus, antibiotic therapy should not be considered in the treatment of biofilm in the petroleum industry except in the very early stage of the planktonic form of the bacteria.

There are multiple cross-talks in the biofilm formation. The most important one is the internal crosstalk between the terminal Pilar proteins and the genetic materials of the same bacterial cell. On the other hand, the external crosstalk is between each bacterial cell and its neighboring ones. The external crosstalk is carried out via (AHL) and (vesicular exocytosis) as will be explained later. The external crosstalk comes secondary to the internal one. Therefore, blockage of the internal crosstalk leads to the abortion of the whole process of biofilm formation at its very early stages via disruption of both the internal and external cross-talks. The mechanics of the internal crosstalk is facilitated by the absence of the nuclear membrane in the bacteria. Therefore, the genetic materials, i.e., bacterial chromosome is very easy to be kept posted about the environment around the bacteria. In the case of an external rough surface, conformational changes occur in the terminal pilus with subsequent electron transport and secondary suction of fluid that passes through the central canal to tell the genetic material to transcribe more hydrophobic proteins necessary for further strong attachment of the terminal pili to the rough surface as shown in the right-side of the illustration of FIG. 3I. On the other hand, with the presence of a smooth surface surrounding the bacteria, the hydrophobic proteins become internalized and are fully surrounded by the hydrophilic ones. The bacteria can only swim and cannot attach to the surface as shown in the left-side illustration in FIG. 3I. Moreover, the central canal is fully blocked by the folded hydrophobic proteins. Subsequently, the water cannot pass through this canal. Therefore, the genetic materials only transcribe the hydrophilic protein necessary for the swimming of the bacterial cell. This crosstalk theory gives us a better and deep explanation of the root causes of biofilm formation. Furthermore, it helps us to break the vicious cycle in biofilm formation as will be described.

Quorum Quenching (QQ) is a process that is opposite to that of Quorum sensing (QS). As stated earlier QS is the threshold number of bacteria that could assemble to form a new biofilm. This is done via (AHL) by which the bacteria of the biofilm could communicate with each other to protect their colony of the biofilm. (QQ) makes the opposite by disturbing this communication. Thus, the bacteria cannot protect their colony and the biofilm would be destroyed by any harsh environment like the high-speed current of oil. (QQ) can be done via many mechanisms that either disruption of AHL communication between the cells (FIG. 3J) or on blocking exocytosis to stop the recruitment of new bacterial cells to the biofilm (FIG. 3K).

QQ via disruption of the AHL communication between the cells is illustrated in FIG. 3J. QQ is achieved with AHL analogs, Lactonases, and Acylases. As is known AHL analogs are chemical structures that are more or less similar to AHL but they cannot do its function. Thus, the bacterial cells cannot communicate with each other, and the biofilm would be disintegrated. Lactonases are certain enzymes that destroy the lactone ring. Therefore, it cannot do its function anymore in bacterial cell-cell communication. Therefore, the biofilm would gradually shrink. Acylases are enzymes that destroy the link between the acyl group and the remaining structure of AHL. The new structure cannot make bacterial cell-cell communication. Therefore, the biofilm is gradually destroyed.

QQ via blocking of exocytosis is illustrated in FIG. 3K. For bacterial cell-cell communication to occur, a process of exocytosis must be established. The suction of fluid via the central canal of the pilus towards the bacterial cell body results in the fluid being mixed with some genetic and protein material from the bacterial cell body. The mixture is sent under the cell membrane of the opposite side of the membrane and sequestrated in a vesicle that is eliminated outside the bacterial cell as a contained cyst. Later, the cyst would rupture and release all its materials that contain chemotactic (attracting) factors that recruit new bacterial cells to the biofilm. Many chemical structures, which include bafilomycin, botulinum toxin B, and/or tetanus toxin, can block the process of exocytosis and can be used to prevent the release of vesicles from the attached bacteria. Thus, there would be no cell-cell communication or recruitment of new bacterial cells. This is very important because that bacterial cells that died in the biofilm would not be replaced by new ones. Therefore, the biofilm would gradually be diminished until it disappears. Moreover, the already present bacterial cells would not communicate with each other to make a synergism of protection of their biofilm. Therefore, the biofilm would not become fully protected from the external harsh environment. Thus, the method of this invention may entail the application of an agent of one or more of bafilomycin, botulinum toxin B, and tetanus toxin to the biofilm.

Persister cells are the cells that minimize their metabolism and enter into a stationary state. These cells could live for an extended period of time, e.g., years, in a harsh environment including resistance to antibiotics. Moreover, these cells could push the antibiotics out of the biofilm. Therefore, the effect of antibiotics may be minimized or even abolished. Furthermore, the resistance of persister cells to antibiotics is several orders of magnitude, e.g., 5,000 times, more than that of bacterial cells of the planktonic stage. Thus, the biofilm could resist antibiotics for decades. Later, when the external environmental factors become favorable, the persister cells can flourish and make new cells in the biofilm. Thus, the biofilm cells could infect other non-infected areas in the tubal system of the oil-carrying pipeline. As stated earlier, the pipeline may be thousands of miles in length, so that the spread of the biofilm may be catastrophic and sometimes impossible to be controlled. Moreover, even when successful, the cost of controlling the infection according to prior art practices is typically exceedingly expensive. Therefore, the best method of management is the prevention of the biofilm formation in the first place, rather than treatment of the already present infection.

The mode of the flow of the oil inside the tubal system of the pipeline is not of a constant speed. In particular, the oil stream runs in layers that slide upon each other. The oil at the center has a higher speed than the oil at the periphery near the inner wall of the pipe or tube carrying the oil. This is called laminar flow and is illustrated in the left side area designated A in FIG. 3E. This factor has significant importance in biofilm formation. The slower speed of oil which is near the inner wall of the tube provides a much better chance for the bacterial cells to make attachments to the inner wall of the tube. The chance of attachment is greatly increased where the inner surface of the wall of the tube carrying the oil is rough. Thus, an ultrasmooth surface of the inner wall of the tube is considered a cornerstone for the prevention of biofilm, the precursor of biocorrosion. This is achieved by the subject invention's use of a PZE coating or lining on the inner surface of the steel oil-carrying tube of the pipeline since PZE is almost always very smooth as will be explained later.

As will be appreciated by those skilled in the art the flow of oil through a pipeline frequently entails, what can be called turbulent flow. Turbulent flow or turbulence entails waves of disturbed circles. This type of flow typically occurs when the pipeline changes its direction and is illustrated in the right-side area designated B in FIG. 3E. This creates a convex area of high pressure and another area, i.e., concave, of low pressure. The turbulent flow occurs from the high to low-pressure areas. After the tube becomes straight again, laminar flow is restored. The importance of this point is that the biofilm tends to occur in the low-pressure area, i.e., the concave area. This is because the area of high pressure washes out the bacteria and prevents their attachment to the steel as illustrated in the area designated B in FIG. 3B. Subsequently, this reduces the incidence of biofilm formation. On the other hand, the low-pressure area shows a sluggish current of the oil that gives the bacteria a chance to attach, whereupon the biofilm would be formed, followed by biocorrosion. One can attempt to minimize the chance of biofilm-induced corrosion in the construction of the pipeline by making it as straight as commercially possible. However, this is not always possible, since sometimes, it is obligatory for the pipeline to change its direction to avoid some obstacles, e.g., a city, sea, river, mountain, etc. That said, every commercially reasonable effort should be made to ensure that the pipeline is as straight as possible commercially to reduce the biofilm formation and subsequent biocorrosion.

The forces responsible for controlling the bacterial biofilm formation, maturation, and the spreading of the infection are the hydrophobic force, the electrostatic force, and the Van Der Waals force. The Van Der Waals force is responsible for the more or less equidistance between the bacterial cells inside the biofilm. This is because every bacterial cell is attracted and repelled to the nearby bacterial cells via an equal force. The attraction force occurs when the bacterial cells diverge away from each other while the repelling force occurs when the bacterial cells get much closer to each other. This causes all bacterial cells to be more or less of the same distance from each other. This force is very essential in maintaining the geometrical structure of the biofilm to grow in an optimal condition, i.e., it allows the bacterial cells to be evenly distributed throughout the biofilm. In other words, it prevents the bacterial cells to be crowded in a certain site of the biofilm and prevents another area to be deficient in the bacterial cells. This force has no more role in the subject invention and will not be discussed further. The hydrophobic (water-hating) force, however, does play a basic role in this invention. As is known it is the force that pushes the molecules or atoms away from water. The nature of this force depends on the electrical charges. It is exactly an electron transport from the metallic surface to the MSCRAMM end of the fimbriae of the bacterial attachment. This creates a secondary electrostatic force between the biofilm and the surface attachment of the metal. The electron is negatively charged and biofilm becomes relatively more negative than the metal. The electrostatic force could be one contributing factor to the firm attachment of the biofilm. This point has a very fundamental importance to the subject invention. By using a material that can change the electrical charges of the lining of the tube, e.g., a PZE material can disturb the hydrophobic forces of bacterial attachment making their dislodgement easier.

Metals in general are good media for biofilm formation with subsequent biocorrosion. This is because metals act as an excellent source of electron transport. This is why they are good conductors of heat and electricity as the peripheral electrons of metals are freely mobile. Moreover, the metal's atomic structure acts as islands of positive nuclei surrounded by seas of negative electrons that are freely mobile, and this is the basis of the metallic bonds. As the tubes of the pipeline are formed mainly from steel, the electron transport at the fimbriae of bacteria could easily occur with subsequent biofilm formation. On the other hand, piezo-electric materials are formed mainly of crystals of alternating atoms of different electronegative momentum (ENM). They have no free electrons. Thus, they are bad conductors of heat and electricity as silicon and ceramic. The most important point of the PZE material is that electron transport at the MSCRAMM could not be accomplished. This is because electron transport is very essential for proper bacterial attachment. Therefore, the bacterial attachment would not occur or at least be minimized, in case of the utilization of the PZE material. Subsequently, the biofilm and biocorrosion would not occur. Moreover, it is well-known that piezo-electric materials produce an electrical gradient difference in response to the application of mechanical stress. Thus, the high speed of the oil current inside the oil-carrying tube of the pipeline will exert mechanical pressure on the inner surface of the tube. Thus, the lining of the inner tube with a PZE material will produce alternation electrical gradient variations that disturb the electron transport of the hydrophobic force that is necessary for bacterial attachment. As such the basal layer attachment would be disturbed and the biofilm would be easily dislodged. Subsequently, biocorrosion could be aborted at its early stages.

Another factor in preventing the occurrence of biofilm growth in pipelines is the rate of flow of oil through the pipeline. High pressure resulting from the pushing or pumping of the oil through the pipeline acts to impede a biofilm from being formed, e.g., the high-speed current of the streaming oil will tend to wash bacteria out of large micro-crevices. The material making up the oil-carrying tubes of the pipeline also plays a factor in the development of MIC. As it is known the tubes carrying oil in a pipeline are either formed of steel or certain types of plastics. Moreover, the petroleum industry seeks to make the inner surface of the oil-carrying tubes as smooth as possible to prevent or at least minimize the friction between the oil and inner walls of the tubes to reduce the cost of pumping the oil through the pipeline. We have found that the smooth surface has a more fundamental function in the prevention of biofilm formation as the bacterial cells cannot readily gain access to a perfectly smooth surface. Even if some bacterial cells succeed to get access to the inner wall, they would be easily washed out under the effect of the high-speed current of the streaming oil. Therefore, the hallmark feature in the prevention of biofilm is the smooth inner wall of the tubes and the high speed of passage of oil inside the tubes. As said earlier, all the PZE materials have a common ultrasmooth surface. Therefore, the PZE materials are beneficial in the prevention of bacterial attachment for 2 main reasons; their atomic structure of absence of free electrons, and their smooth surface.

The subject invention prevents biofilm before its formation in the petroleum pipeline or other oil-carrying conduit. It combines the following criteria: (1) the mechanism of conversion of the planktonic bacteria to biofilm; (2) the coordination of the bacterial components inside the biofilm via AHL; (3) control of the size of micro-crevices in the lining of the oil-carrying tube of the pipeline; (4) the mechanisms of resistance of biofilm to antibiotics; (5) the importance of the persister cells in the dormancy of biofilms for long periods of time, e.g., years or even decades if the conditions are unfavorable; and (6) the forces that control biofilm (hydrophobic, electrostatic, and Van Der Waals forces).

Of the above, the microscopic rough surface (e.g., the micro-crevices) of the inner layer of the tubes is the initiating factor of biofilm formation. In particular, the inner wall of the oil-carrying tubes of pipelines includes micro-crevices, like that shown in the sketch of FIG. 3D, that are not detectable by the naked eye or even by low-power microscopes. Those micro-crevices are in the range of 20-50 μM as illustrated in the area designated C in FIG. 3B. Crevices of this size are considered optimal for the bacteria to hide away from the washing effect of the high-speed passage of oil. Moreover, the bacteria coalesce with each other until they reach a certain threshold of number, whereupon a biofilm is created by the process of quorum sensing (QS) as mentioned earlier. Crevices smaller than 10 μM are too small to fit the threshold number of the bacterial cells to assemble a new biofilm. This is if we put into consideration that the average size of the bacterial cell is 1 μM. This is illustrated in the area designated A in FIG. 3B. The high-speed current of the oil's stream does not give the bacteria a chance to settle down to the bottom of those very small micro-crevices due to their narrow opening or width. In other words, the narrow opening of micro-crevices coupled with the high speed of the oil stream ensures that a very limited number of bacteria have a chance to descend to the bottom of the micro-crevices. The probability of this limited number of bacteria to communicate with each other and to produce a biofilm is hence very low. This is consistent with quorum sensing (QS). On the other hand, if the micro-crevices' sizes are more than 50 μM in width, they have a common opening with the mainstream of the flow. Thus, the force of the stream inside the crevice is high enough to destroy a newly borne biofilm at its beginning or to wash away any biofilm that had started as illustrated in the area designated as B in FIG. 3B. As indicated above the early stage of bacterial attachment is reversible and can be easily washed out, particularly if the crevice has a wide opening since the wide opening causes turbulent flow that washes out the biofilm at its early stage, i.e., the reversible stage.

Micro-crevices in the range of 20-50 μM are optimal for biofilm formation since enough bacteria will have a chance to descend to the bottom of the crevice without being washed out due to the absence of turbulent flow. Thus, the bacteria reaching the bottom of the crevice have a chance to assemble with each other to make the biofilm. Most of the biofilms proceed from early reversible attachment to late irreversible attachment. Thus, the biofilm could protect itself against the high-speed current of the flowing oil. Once the bacterial attachment becomes irreversible, the biofilm proceeds to the maturation stage and it becomes large enough to start the process of the infection of other areas of the downstream tubes via the spreading of the planktonic bacterial cells from the top of the biofilm.

In view of the above, if the inner layer of the tubal system of the pipeline is smooth at the microscopic level, this biofilm would not be formed. Therefore, the main preventive effect of biofilm formation is the lining of the inner wall of the tubes of the pipeline with a material that has no appreciable micro-crevices into which the bacteria can gain access and settle. This is accomplished through the utilization of the inner wall of the tube with a thin film of piezo-electric material.

The most important layer of the biofilm is the basal layer of the bacteria that attach firmly to the rough surface of the steel tube via hydrophobic and subsequent electrostatic forces. These forces depend on the electron transport from the metallic surface to the MSCRAMM end of the fimbriae of the bacteria. The PZE material coating that is applied on the inner surface of the steel tubes of the pipeline in accordance with this invention has the property of converting some applied mechanical stress into an electrical gradient difference. Thus, a lining of the inner layer of the tube with a thin layer of PZE material has the effect of disturbing the hydrophobic force of the basal layer of the bacterial attachment. The PZE materials have an inhibitory effect on this electron transport with subsequent failure or at least difficulty of bacteria cells to get an attachment to the surface. The most important property of the PZE materials is their common smooth surface e.g., ceramic, silicone, etc. Thus, the bacterial cells have a very hard time in getting a firm attachment to the surface of the PZE material. This means that the early reversible attachment stage may not occur. Consequently, the following stages of the irreversible attachment and maturation stages would not occur. This is simply because they depend on the early reversible stage.

Furthermore, the PZE materials fill the cavity of the metallic micro-crevice. Subsequently, the micro-crevice is converted into a shallow groove as illustrated by the area designated B in FIG. 3C so that the high speed of the oil flowing can easily reach the bottom of the groove, whereupon the bacterial cells are easily wiped out under the effect of the high-speed current of the oil flow.

It could be summarized that the PZE materials prevent or hinder biofilm formation due to the main following points: (1) they have an electrical property that prevents electron transport from the PZE material to the terminal ends of the bacterial pili. This is because there are no free electrons in the PZE materials. Moreover, (2) the PZE materials under the repeated and continuous mechanical stress of the flowing oil show electrical gradient differences that disturb the process of electron transport; (3) they are almost always very smooth, whereupon the smooth surface reduces the capacity of the bacteria to get a firm attachment to the PZE lining; and (4) the PZE material fills the underlying micro-crevices which converts them into shallow grooves, whereupon the high-speed current of the oil enables the oil to reach the bottom of this shallow groove to easily wash out the bacteria from the bottom of the groove before the formation of the irreversible attachment stage as illustrated in FIG. 3C.

The following are common piezoelectric materials that can be used to form the lining or coating on the inner surface of the oil-carrying tube of the pipeline: silicon oxide (crystalline form); ceramic (aluminum oxide); polyvinylidene fluoride (PVDF); or zinc oxide. Others, such as lead zirconate titanate, quartz, lead titanate, barium titanate, gallium nitride, aluminum nitride, and others are also contemplated. The PZE materials may be coated or otherwise applied to the inner surface of the oil-carrying tube in any conventional manner. The thickness of the PZE coating is at least approximately 2 mm thick.

As should be appreciated by those skilled in the art from the foregoing while the size of the micro-crevices is a factor in the propensity for the formation of bacterial biofilm-induced corrosion, the application of a coating of PZE in accordance with this invention should in-and-of itself preclude or otherwise inhibit the growth of the bacterial biofilm irrespective of the size (width) of the micro-crevices in the steel pipes or tubes. There are two main reasons, namely, physical, and chemical. Insofar as the physical reason is concerned, PZE materials are generally very smooth and thus tend to occlude any deep micro-crevices, e.g., they are transformed into shallow grooves that cannot protect the bacteria from the high stream of oil current. In the early stage, bacterial attachment is reversible and weak as discussed in detail above. Thus, the bacteria need shelters for their protection until they enter the irreversible stage where they can protect themselves from being washed away with the flowing oil. Insofar as the chemical reason is concerned, PZE materials are mainly formed of crystals where one atom of high electronegative momentum (ENM) is alternating with another atom of low electronegative momentum (ENM) so that there are no free electrons as in the case of metals as discussed above. The irreversible attachment of the bacterial biofilm depends on the hydrophobic force. This force depends on the electron transport from the metallic end to the MSCRAMM bacterial end. As metals have free electrons, an irreversible attachment could occur. In contradistinction with the PZE materials of the subject invention lining the steel tubes, there will be no free electrons, such that irreversible attachment of the bacteria is precluded.

In short, the use of PZE materials as the lining of the oil-carrying pipes or tubes as contemplated by this invention prevents bacterial biofilm both physically and chemically. It must be noted that the physical prevention of the biofilm is done in the early reversible stage of attachment while the chemical prevention of the biofilm is done in the later irreversible stage of attachment. This explains the high efficacy of the PZE material in the prevention of biofilm formation by the abortion of the process at two consecutive levels: the reversible and the irreversible ones.

As mentioned earlier, the catastrophic problem of biofilm-induced corrosion is addressed by the subject invention's three above-mentioned lines of treatment. In particular, the most important line of treatment is hindering the attachment of the basal layer of bacterial biofilm with the inner wall of the pipeline. By doing so the subject invention either aborts the attachment in the first place or makes the attachment very weak to the extent that it could not establish the biofilm. The second line of treatment in the order of importance, i.e., the blockage and disruption of the communication between the bacterial cells inside the biofilm ensures that those cells could not help each other to maintain the integrity of the biofilm. Therefore, the biofilm could be disintegrated and disrupted. This line of treatment can be accomplished via the application of an agent such as acyl-homoserine lactone analog, i.e., (AHL) analog, lactonases, and acylases as shown in FIG. 3J and discussed above. The third line of treatment in order of importance, i.e., the blockage of exocytosis, aids the first two lines of treatment. In particular, the bacterial cells of the biofilm absorb the fluid in the biofilm. Then, they mix this fluid with some genetic materials and parts of bacterial proteins. The combination would form a viscid solution that is sent under the bacterial membrane and is prepared to be excreted outside the cell by the process of exocytosis. As is known exocytosis is the fusion of secretory vesicles with the plasma membrane and results in the discharge of vesicle content into the extracellular space and the incorporation of new proteins and lipids into the plasma membrane. This excreted fluid would be in a vesicle that ruptures and release its contents, which have chemotactic factors, i.e., substances that can attract other bacterial cells to this site and the biofilm would increase in size. Blockage of exocytosis can stop all these steps as shown and described with reference to FIG. 3K.

It must be emphasized that the first line of treatment or step is the most important one in the prevention and control of the biofilm, because it prevents the biofilm from its occurrence in the first place. On the other hand, the second and third lines of treatment are needed after the biofilm is already present. Therefore, they act as an adjuvant therapy for the first line of treatment. This means great attention must be paid to the first line of treatment more than the second and third lines of treatment.

It must be pointed out at this juncture that while the discussion above has focused on pipelines including steel tube sections for carrying liquid oil, the subject invention is not so limited. Thus, the subject invention has applicability for any structure carrying or holding liquid oil and which could be subject to bacterial biofilm-induced corrosion or blockage. This is because the storage containers have more incidence of corrosion than the pipelines. This is due to the absence of the flow of oil's current that may wash the biofilm in its very early stage of reversible attachment. With respect to pipelines, the incidence of biofilm formation could be reduced if the inner surface of the oil-carrying tube or pipe of the pipeline is made ultrasmooth and more or less straight with minimal change in its direction.

In summary, all the already present methods of the treatment of biocorrosion in the oil industry are very expensive and inevitably fail because the root causes of the problem are not corrected. The bacterial cells of the biofilms have no nucleus but they have genetic materials floating in the cytoplasm without a nuclear membrane. This explains the free communication between the genetic materials and terminal pilar proteins and the cell membrane. The genetic material acts as the mediator and the regulator between pilar proteins and the cell membrane in two axes. The most important step of biocorrosion is bacterial attachment via their pilar protein conformation on attachment on the relatively rough surface of the inner membrane of the tube. Therefore, suppression of this very early step which the subject invention achieves should be considered the treatment of choice for the eradication of the biocorrosion from its roots. To that end, the subject invention concentrates on the molecular mechanics of the conformational changes in the terminal pili of the infecting bacteria. The starting point of the biofilm formation and its progress depends on the changes that occur in the proteins of terminal pili. The success to block this step of early attachment of the bacterial pili to the inner wall of pipelines would prevent all the subsequent steps of biofilm formation. Therefore, great attention must be paid to the molecular mechanics of terminal pili and the mechanism of their attachment to the inner wall of pipelines to abort the whole process at its early stage.

It may not be practical to replace all pipelines with new ones that are lined with PZE material to avoid biofilm. The more appropriate and cost-effective solution is to replace every leaked segment with a new one that is lined with PZE material. In the long run, the whole system would be fixed. On the other hand, the adjuvant therapy of the blockers of (AHL) and (exocytosis) must be started as soon as possible to replace the already present antibiotics therapy.

Without further elaboration, the foregoing will so fully illustrate our invention that others may, by applying current or future knowledge, adopt the same for use under various conditions of service.

We claim:

1. A method of precluding or minimizing bacterial biofilm-based corrosion of a carrier or holder of liquid petroleum comprising:

providing a hollow structure which will be exposed to a flow of liquid petroleum, said hollow structure being formed of steel, said hollow structure having an inner surface including micro-crevices, said inner surface being coated or lined with a piezo-electric material, wherein said micro-crevices have a width of less than approximately 10 μM or greater than approximately 50 μM.

2. The method of claim 1, additionally comprising applying a force to the liquid petroleum to result in turbulent flow in said micro-crevices which are greater than approximately 50 μM.

3. The method of claim 1, wherein said piezo-electric material is selected from the group comprising: silicon oxide, ceramic, polyvinylidene fluoride (PVDF), or zinc oxide.

4. The method of claim 3, additionally comprising applying a force to the liquid petroleum to result in turbulent flow in said micro-crevices which are greater than approximately 50 μM.

5. The method of claim 1, wherein said piezo-electric material is at least approximately 2 mm thick.

6. The method of claim 1, wherein said carrier comprises a petroleum pipeline, and wherein said hollow structure comprises a pipe or tube.

7. The method of claim 6, wherein said method comprises causing said liquid petroleum to flow through said pipe or tube.

8. The method of claim 1, where said biofilm includes bacterial cells and wherein said method additionally comprises blocking and disrupting communication between the bacterial cells in the biofilm.

9. The method of claim 8, wherein said blocking and disrupting communication between the bacterial cells in the biofilm is accomplished by use of an agent of one or more of acyl-homoserine lactone analogs, lactonases, and acylases.

10. The method of claim 8, wherein said bacteria cells are capable of exocytosis, and wherein said method additionally comprises blocking exocytosis among the bacteria cells.

11. The method of claim 10, wherein said blocking exocytosis among the bacteria cells is accomplished by use of an agent one or more of bafilomycin, botulinum toxin B, and tetanus toxin.

* * * * *